United States Patent
Yuyama et al.

(10) Patent No.: US 7,333,938 B1
(45) Date of Patent: Feb. 19, 2008

(54) APPARATUS FOR SUPPORTING INJECTION MIXING WORK

(75) Inventors: Hiroyuki Yuyama, Toyonaka (JP); Keita Yasuoka, Toyonaka (JP)

(73) Assignee: Yuyama Mfg., Co., Ltd., Osaka-Fu (JP)

( * ) Notice: Subject to any disclaimer, the term of this patent is extended or adjusted under 35 U.S.C. 154(b) by 0 days.

(21) Appl. No.: 09/559,401

(22) Filed: Apr. 26, 2000

(30) Foreign Application Priority Data

Apr. 27, 1999 (JP) ................... 11-119719

(51) Int. Cl.
*A61B 5/00* (2006.01)
*G06F 19/00* (2006.01)

(52) U.S. Cl. ........................................... 705/3
(58) Field of Classification Search ............... 705/2, 705/3; 600/300
See application file for complete search history.

(56) References Cited

U.S. PATENT DOCUMENTS

| | | | | |
|---|---|---|---|---|
| 5,002,055 A | * | 3/1991 | Merki et al. ............... | 600/345 |
| 5,281,396 A | * | 1/1994 | Leissing et al. .......... | 422/82.09 |
| 5,643,212 A | * | 7/1997 | Coutre et al. ............. | 604/131 |
| 5,781,442 A | * | 7/1998 | Engleson et al. .......... | 700/214 |
| 5,845,255 A | * | 12/1998 | Mayaud ..................... | 705/3 |
| 5,925,014 A | * | 7/1999 | Teeple Jr. .................. | 358/1.15 |
| 6,070,761 A | * | 6/2000 | Bloom et al. ............... | 222/81 |
| 6,308,109 B1 | * | 10/2001 | Yuyama et al. ............ | 700/228 |

FOREIGN PATENT DOCUMENTS

JP   8-212271 A   8/1996

OTHER PUBLICATIONS

Cobb, Stability of Fludarabine Phosphate, Pentostatin, and Amsacrine in Commonly Used Infusion Solutions and After Filtration, and Osmolality of Various Constituted Chemotherapeutic Agents, 1995, Disertations Abstracts International, vol. 5610B, p. 5437.*

* cited by examiner

*Primary Examiner*—C. Luke Gilligan
(74) *Attorney, Agent, or Firm*—Wenderoth, Lind & Ponack, L.L.P.

(57) ABSTRACT

An apparatus for supporting injection mixing work comprises a memory for storing data for supporting injection mixing work, a display for displaying the data stored in the memory and a controller for controlling the display. The memory has a patient predictability data file for storing patient predictability data including at least patient predictable information, an injection prescription data file for storing injection prescription data corresponding to the patient predictability data, and a combination related data file for storing combination related data corresponding to each injection of the injection prescription data. The controller displays the predictability data stored in the patient predictability data file according to both the injection prescription data corresponding to the patient predictability data and the combination related data of each injection included in the injection prescription data.

17 Claims, 13 Drawing Sheets

Fig.2

<INJECTION PRESCRIPTION FILE>

| INJECTION PRESCRIPTION DATA #N | INJECTION PRESCRIPTION DATA #(N+1) |
|---|---|
| (INPUT DATE) 19981218<br>(PATIENT No.)<br>93026581 \| 60<br>601<br>01<br>0102<br><br>(DATE OF PRACTICE)  (MIXING RESULT FLAG)<br>19981218 \| 0<br>(PRESCRIPTION No.)<br>1 \| INJA \| 2 \| A<br>INJB \| 1 \| V<br>INJC \| 1 \| A<br>INJD \| 1 \| V<br>INJE \| 0.5 \| A<br>/02<br>*101 | (INPUT DATE) 19981218<br>(PATIENT No.)<br>95001631 \| 70<br>702<br>02<br>0203<br><br>(DATE OF PRACTICE)  (MIXING RESULT FLAG)<br>19981218 \| 0<br>(PRESCRIPTION No.)<br>1 \| INJD \| 2 \| V<br>INJE \| 1 \| A<br>/02<br>*201 |

Fig. 3

<INJECTION PRESCRIPTION DATA INPUT>   1998.12.18

| | |
|---|---|
| PATIENT No. | 93026681 |
| PATIENT NAME | TAROU YAMADA |
| SEXUALITY | 1 MAN |
| BIRTH | 3 1945.05.26 |
| AGE | 053 YEARS OLD 07 MONTH |

| | |
|---|---|
| WARD | 60 6 FLOOR WARD |
| SICKROOM | 601 |
| CLINIC | 01 MEDICINE |
| DOCTOR | 0102 HANAKO KAWAKAMI |

DATE OF PRACTICE 1998.12.18          MIXING RESULT 0 NOT MIXING

| PRESCRIPTION No. | CODE | MEDICAMENT NAME/ MANIPULATION*USAGE | | ONE DOSE RATE |
|---|---|---|---|---|
| 1 | INJA | INJECTION A | 10ml | 2A |
| | INJB | INJECTION B | 500ml | 1V |
| | INJC | INJECTION C | 20mg2ml | 1A |
| | INJD | INJECTION D | 500mg | 1V |
| | INJE | INJECTION E | 1ml | 0.5A |
| | /02 | <DRIP> | | |
| | *101 | ONCE, MORNING | | |

NEW INPUT          INPUT OK    CANCEL          END OF MIXING WORK

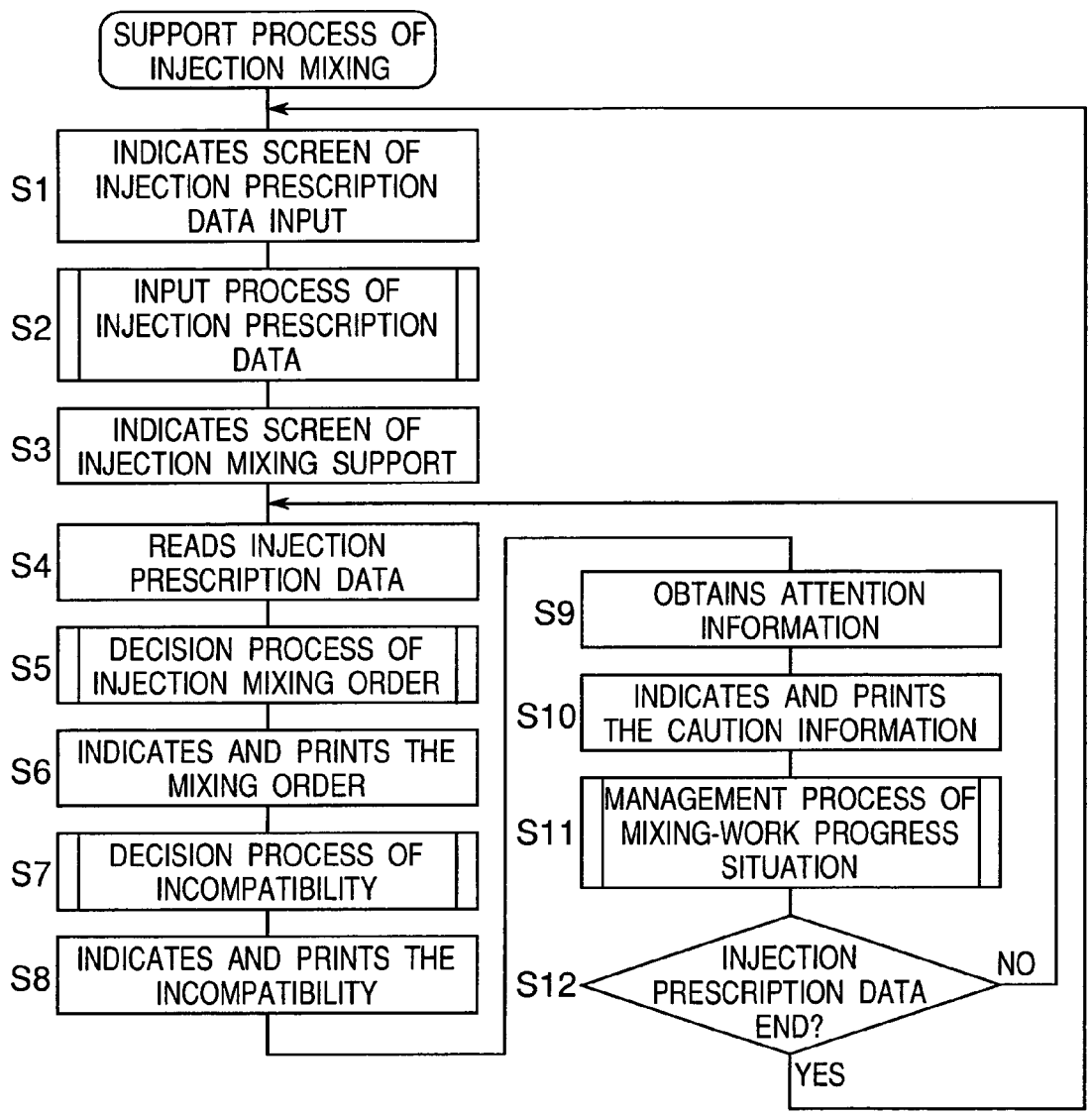

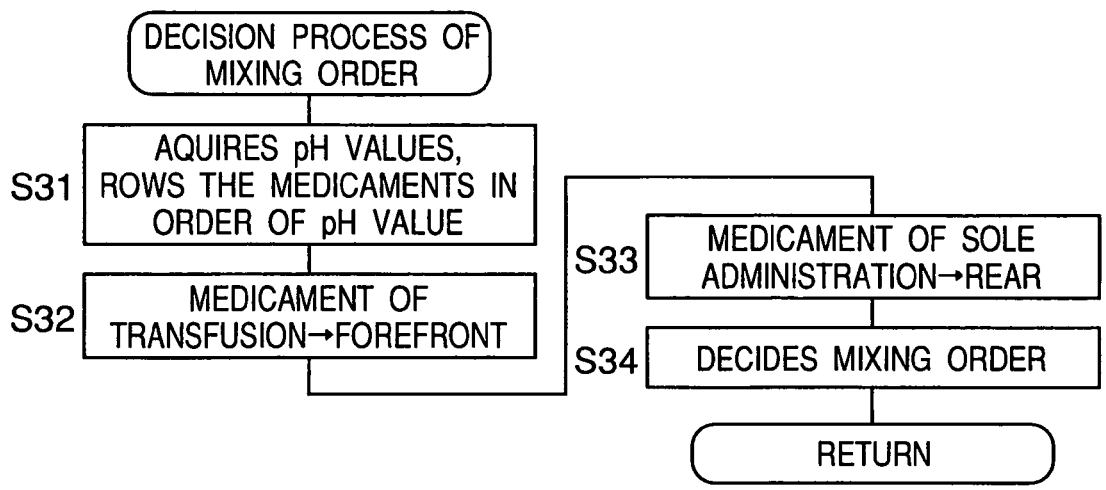
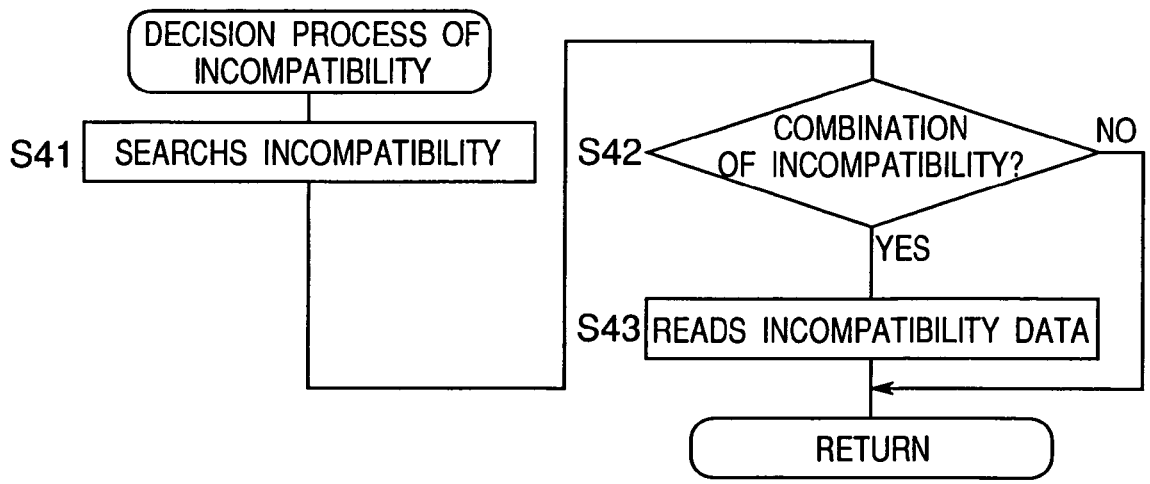

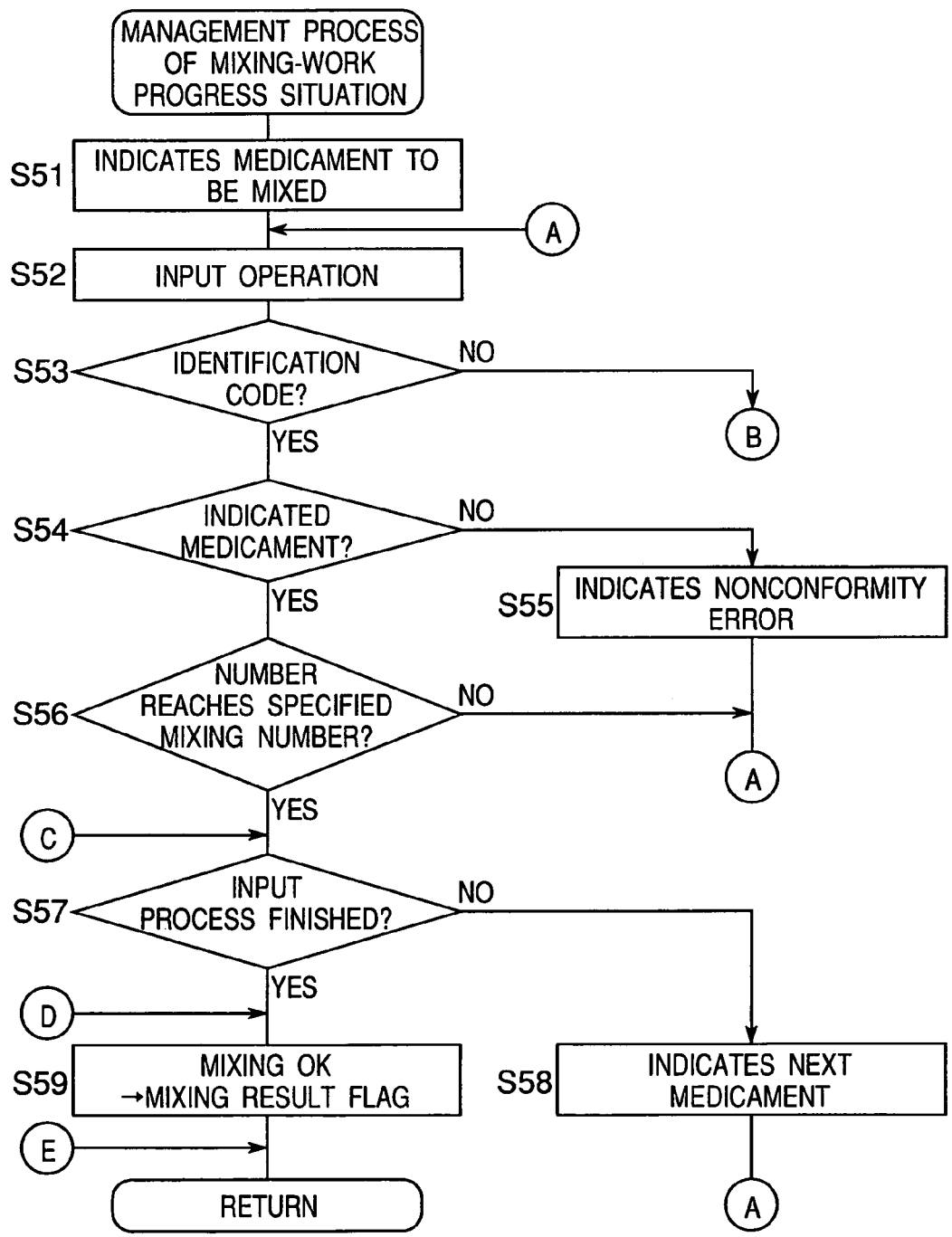

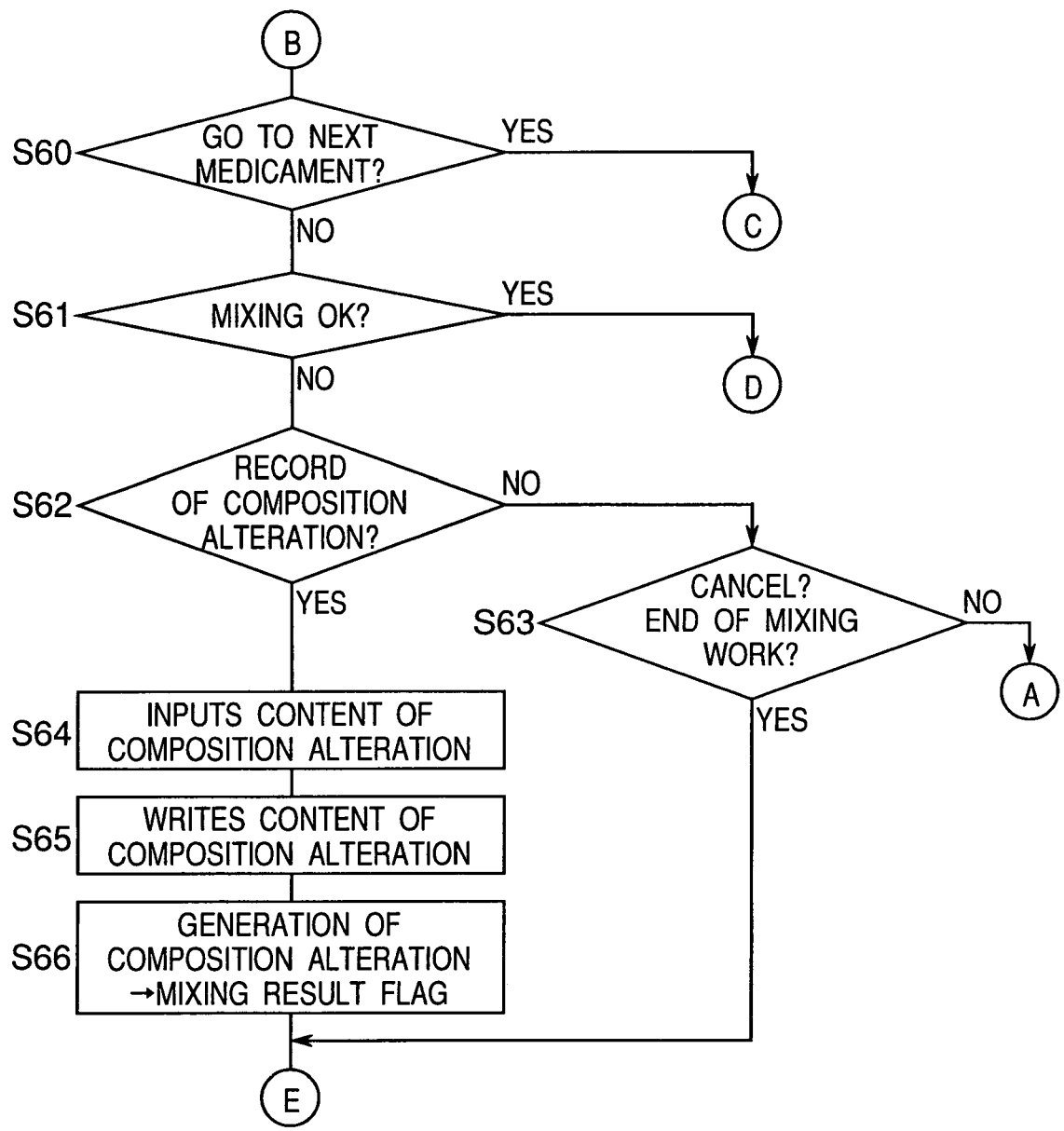

Fig. 10

<INJECTION MIXING SUPPORT>  1998.12.18

| | |
|---|---|
| PATIENT No. | 93026681 |
| PATIENT NAME | TAROU YAMADA |
| SEXUALITY | 1 MAN |
| BIRTH | 3 1945.05.26 |
| AGE | 053 YEARS OLD 07 MONTH |

| | |
|---|---|
| WARD | 60 6 FLOOR WARD |
| SICKROOM | 601 |
| CLINIC | 01 MEDICINE |
| DOCTOR | 0102 HANAKO KAWAKAMI |

DATE OF PRACTICE 1998.12.18
PRESCRIPTION No.1 MANIPULATION : <DRIP> USAGE : ONCE MORNING

| pH | TRANSFUSION | MIXING CAUTION | INCOMPATI- BILITY | MIXING ORDER | MEDICAMENT NAME | | ONE DOSE RATE | NUMBER | STABILITY TIME |
|---|---|---|---|---|---|---|---|---|---|
| 5.5 | TRANSFUSION | | | | INJECTION B | 500ml | 1V | 1 | |
| ★ 4.0 | | ○ | △ | 1 | INJECTION A | 10ml | 2A | 1 | 2 |
| 6.2 | | | △ | 2 | INJECTION E | 1ml | 0.5A | | |
| 8.0 | | ○ | SOLE | | INJECTION C | 20mg2ml | 1V | | |
| 3.6 | | | | 3 | INJECTION D | 500mg | 1A | | |

| GO TO NEXT MEDICAMENT | | MIXING OK | CANCEL | END OF MIXING WORK |
|---|---|---|---|---|
| PRINT | RECORD OF COMPOSITION ALTERATION | | | |

Fig.11

| PRESCRIPTION No. | CODE | MEDICAMENT NAME/ MANIPULATION*USAGE | | ONE DOSE RATE |
|---|---|---|---|---|
| 1 | ⋮ | ⋮ | | ⋮ |
| 2 | INJA<br>INJB<br>/02<br>*103 | INJECTION A<br>INJECTION B<br><DRIP><br>ONCE, MORNING | 10ml<br>500ml | 2A<br>1V |

Fig.12

<CONTENT OF COMPOSITION ALTERATION IN INCOMPATIBILITY>

| A MEDICAMENT NAME | B MEDICAMENT NAME | INCOMPATIBILITY | CONTENT OF COMPOSITION ALTERATION |
|---|---|---|---|
| INJECTION A 10ml | INJECTION C 20mg 2ml | △ | AFTER 6HOURE, SURVIVAL TITER 91% |

PRINT  CANCEL

Fig.13

| MEDICAMENT NAME | | ATTENTION INFORMATION |
|---|---|---|
| INJECTION E | 1ml | SHADING SHOULD BE DONE DURING DRIP. |
| | | WATCH THE SHOCK DURING ADMINISTRATION. |
| INJECTION D | 500mg | INJECTION VELOCITY TO BE BELOW 50mg PER MINUTES. |

<ATTENTION INFORMATION>

[PRINT] [CANCEL]

Fig.14

<RECORD OF COMPOSITION ALTERATION>

TERMINAL ID        03
GENERATION DATE    1998.12.18   08:00
RECORDER           6007  YOSHIKO KAWAMURA

CONTENT OF COMPOSITION ALTERATION (COMMENT)

TURBIDITY

[ RECORD OK ]   [ CANCEL ]

APPARATUS FOR SUPPORTING INJECTION MIXING WORK

BACKGROUND OF THE INVENTION

The present invention relates to an apparatus for supporting injection mixing work, particularly an apparatus for supporting work for mixing a plurality of injections in a medical agency such as a hospital and clinic.

It is often conducted, in a medical work, to mix a plurality of injections in order to dose it to a patient. Almost all of the injection mixing works are conducted by a nurse in a nurse station in a hospital.

In the injection mixing works, it is necessary to select a proper injection and conduct the work in a proper order so as not to cause an appearance alteration such as turbidity, sedimentation and so on, and a composition alteration such as separation of a component, decrease of content and titer and so on.

Thus, the nurse needs to have information about the proper mixing of the injection. Such information is described in the literature but the amount thereof is huge. In addition, the information varies and is difficult to understand.

There has been proposed an approach to make a list so that the nurse can easily understand the combination of injections for proper mixing. In this case, it is difficult to find out a combination of injections among a number of combinations of injections. Therefore, in actual practice, the nurse inquires of a pharmacist about the propriety of a combination of injections, thereby resulting in an increased amount of work time and thus delaying work.

Furthermore, there are many matters in mixing injections, for example, mixing (combination) order, composition alteration, side effect, dosing method, stability after dissolution and so on, but everybody is not always familiar with such matters. Therefore, it is difficult to mix the injections efficiently and certainly. If the injections are mixed in error, such a mixture should be discarded.

SUMMARY OF THE INVENTION

It is an object of the present invention to provide an apparatus for supporting injection mixing work through which everybody can mix the injections efficiently and certainly.

According to the present invention, there is provided an apparatus for supporting injection mixing work, comprising:

a memory for storing data for supporting injection mixing work, the memory having a patient predictability data file for storing patient predictability data including at least patient predictable information, an injection prescription data file for storing injection prescription data corresponding to the patient predictability data, and a combination related data file for storing combination related data corresponding to each injection of the injection prescription data;

a display for displaying the data stored in the memory; and a controller for controlling the display to display the patient predictability data stored in the patient predictability data file according to both the injection prescription data corresponding to the patient predictability data and the combination related data of each injection included in the injection prescription data.

According to the present invention, because several kinds of data, with respect to the combination of injections, are displayed on the display, necessary information can be surely and quickly obtained, thereby enhancing the efficiency of the mixing work of injections.

Preferably, the combination related data file of the memory stores pH-values data for each injection, wherein the controller decides a mixing order of the injections contained in the injection prescription data in accordance with the pH-values data, and wherein the controller displays the mixing order on the display. Thus, the mixing order of the injections can be automatically decided, thereby further enhancing the efficiency of the mixing work of injections.

Preferably, the combination related data file of the memory stores differentiation data for differentiating a transfusion and a solely administrated medicament, and wherein the controller classifies the injection contained in the injection prescription data for a patient into transfusion or solely administrated medicament in accordance with the differentiation data and displays classified injection on the display. Thus, the medicament which can not be mixed can be differentiated, thereby further enhancing the efficiency of the mixing work of injections.

Preferably, the combination related data file of the memory stores incompatibility data showing whether or not a combination of two kinds of injections is incompatible, wherein the controller decides whether or not a combination of two kinds of injections contained in the injection prescription data for a patient is incompatible in accordance with the incompatibility data, and wherein the controller displays such decisions to the incompatibility of combining different kinds of injections on the display. Thus, necessary information with respect to the incompatibility of the combination of different kinds of injections can be surely and quickly obtained, thereby preventing the generation of an injection which will not be able to be used as a result of mixing incompatible injections.

Preferably, the combination related data file of the memory stores attention information data related to each injection, and wherein the controller displays an attention information in the attention information data on the display corresponding to each injection of the injection prescription data. Thus, when mixing the injections, detailed attention information can be confirmed in accordance with the displayed contents on the display, thereby enabling the operator of the apparatus to more effectively conduct the mixing work.

Preferably, the apparatus further comprises a reader for reading an identification code for identifying each injection, wherein the controller displays a progress situation of the mixing work on the display in accordance with the identification code as read by the reader when conducting the mixing work of the injection. Thus, the mixing work can be effectively conducted with the displayed contents on the display confirming the progress situation, thereby enabling the operator of the apparatus to more effectively conduct the mixing work.

Preferably, when conducting the mixing work of the injection in the mixing order as decided in accordance with the pH-values data, the controller decides whether the injection is proper or not in accordance with the identification code of the injection as read by the reader, and if the injection improper, the controller displays such information on the display. Thus it is possible to properly conduct the mixing work without failing, thereby surely preventing an error in the mixing procedure.

Preferably, the apparatus further comprises an input device which is used to input new incompatibility data in addition to the incompatibility data stored in the combination related data and to store it in the combination related data of the memory. Thus, it is possible to effectively use the information of new incompatibility data at the next mixing work, thereby preventing a waste of an injection.

Preferably, the apparatus further comprises a reader for reading a prescription identification code for identifying each injection prescription data, wherein the controller reads the corresponding injection prescription data in accordance with the prescription identification code and displays it on the display. Thus, it is possible to prevent the delay of an input operation, thereby further enhancing the efficiency of mixing work of injections.

BRIEF DESCRIPTION OF THE DRAWINGS

Further objects and advantages of the present invention will become clear from the following description when taken in conjunction with the preferred embodiments thereof with reference to the accompanying drawings, in which:

FIG. 2 is a diagram showing an injection prescription file of the apparatus of FIG. 1;

FIG. 3 is a front view of an injection prescription data input screen displayed on a liquid crystal display of the apparatus of FIG. 1;

FIG. 4 is a flow chart showing a support process of injection mixing as executed by a central processing unit of the apparatus of FIG. 1;

FIG. 6 is a flow chart showing a decision process of a mixing order of FIG. 4;

FIG. 7 is a flow chart showing a decision process of an incompatibility of FIG. 4;

FIG. 8 is a flow chart showing a management process of a mixing-work progress situation of FIG. 4;

FIG. 9 is a flow chart continued from FIG. 8;

FIG. 10 is a front view of an injection mixing support screen displayed on the liquid crystal display of the apparatus of FIG. 1;

FIG. 11 is a front view of the injection prescription data input screen of FIG. 3 with two prescriptions inputted;

FIG. 12 is a front view of a screen showing a composition alteration in the incompatibility displayed on the liquid crystal display of FIG. 1;

FIG. 13 is a front view of a screen showing a content of attention information displayed on the liquid crystal display of FIG. 1; and FIG. 14 is a front view of a screen showing a record of composition alteration displayed on the liquid crystal display of FIG. 1.

DETAILED DESCRIPTION OF THE PREFERRED EMBODIMENTS

Figure 1:
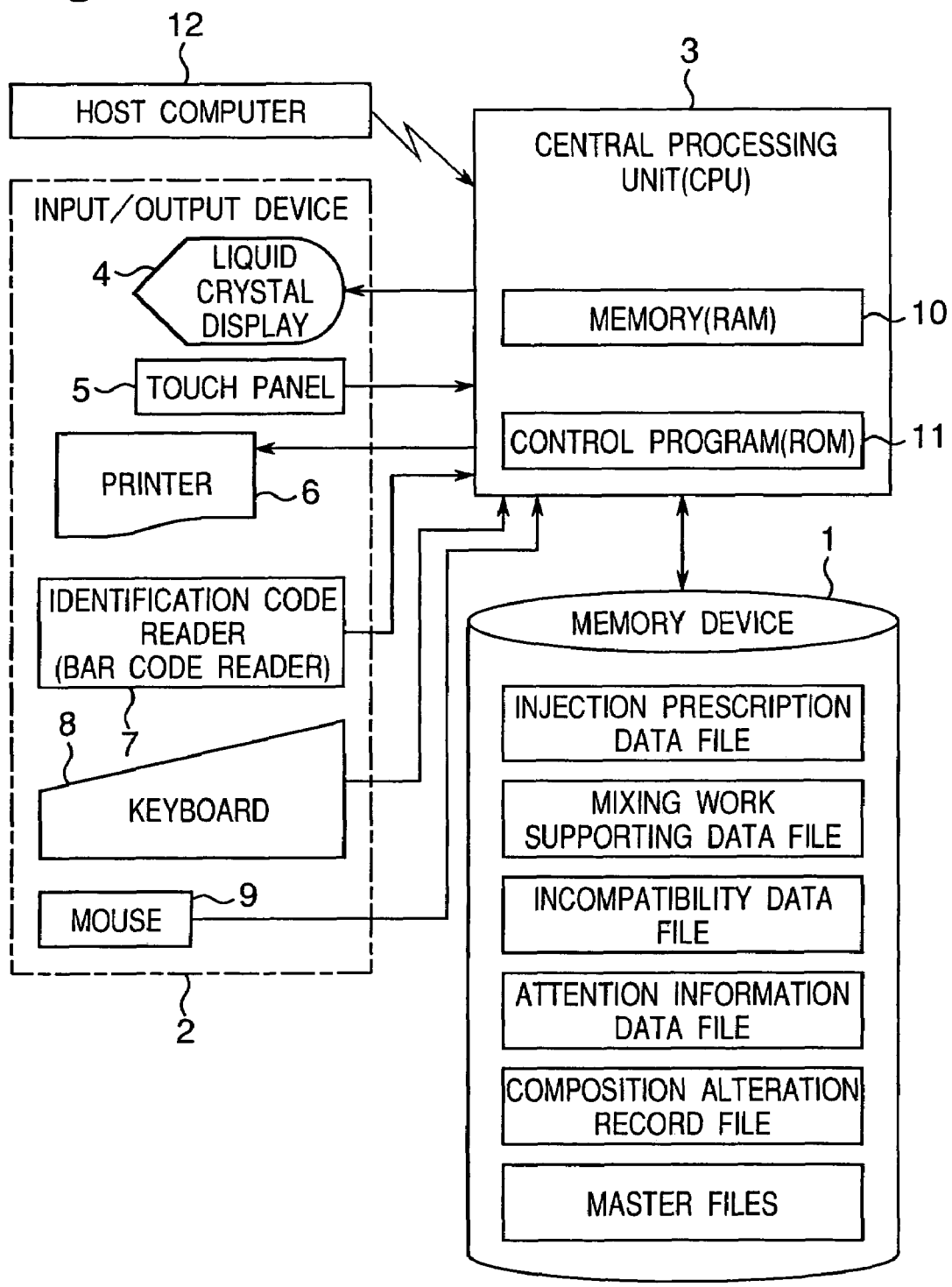
FIG. 1 is a block diagram of an apparatus for supporting injection mixing work according to the present invention.

FIG. 1 shows a block diagram of an apparatus for supporting injection mixing work according to the present invention. The apparatus for supporting injection mixing work comprises a memory device 1, an input/output device 2 and a central processing unit 3.

The memory device 1 includes an injection prescription data file, a mixing work supporting data file, an incompatibility data file, an attention information data file, a composition alteration record file, and several kinds of master files.

The injection prescription data file stores, as shown in FIG. 2, only the code data of the injection prescription data (FIG. 3) for the one day on which an injection is conducted.

Concretely, the code data includes an input date, a patient number, the date of practice, a mixing result flag and a prescription number.

The input date and the date of practice are represented by numbers showing the year, month and day. The patient number, which is unique for each patient, comprises a patient code represented by eight figures and code numbers corresponding to the ward, sickroom, clinic and doctor. The mixing result flag comprises code numbers 0, 1 and 2 allocated for "not mixing", "mixing OK" and "generation of composition alteration", respectively. The mixing result flag is used as a discriminant or criterion when reading the injection prescription data as described hereinafter. The prescription number comprises code numbers allocated for each injection prescription data. Thus, data is read from the several kinds of master files in accordance with these code data.

Generally, the doctor conducts the direction of injection prescriptions for several days together. In conformity with this practice, therefore, the injection prescriptions for several days are also stored together in the injection prescription data file. In the case where the doctor conducts the direction of an injection prescription one after another due to a change in the condition of the patient, a plurality of different injection prescription data would be present for the same patient and for the same injection day.

The injection prescription data can be inputted by a keyboard 8 or a mouse 9, or otherwise can be automatically read from the host computer 12. The mixing work supporting data file stores all kinds of necessary data to operate the apparatus for supporting injection mixing work. Such data is set for each medicament code as shown in Table 1.

TABLE 1

| Medicament Code | pH-value | Transfusion Flag | Mixing Attention Flag | Stability Time (H) after Dissolution |
|---|---|---|---|---|
| INJE (Injection E) | 6.2 | 0 | 0 | |
| INJA (Injection A) | 4.0 | 0 | 1 (Mixing Attention) | |
| INJC (Injection C) | 8.0 | 0 | 0 | |
| INJD (Injection D) | 3.6 | 0 | 2 (sole Administration) | 2 |
| INJB (Injection B) | 5.5 | 1 (Transfusion) | 0 | |

In Table 1, the medicament code is expressed by abbreviation so that the pharmacist can easily input it and the quantity of data can be reduced. For example, the medicament code of injection E is expressed by INJE. The medicament code is the same as one stored in a medicament master file which will be described hereinafter.

The pH-value is an index number of a hydrogen ion within the medicament. The injection is apt to cause composition alteration based on the pH-value.

The transfusion flag serves to show whether the medicament is transfusion or not. If the medicament is transfusion, then the transfusion flag is "0"; and if the medicament is not transfusion, then the transfusion flag is "1". In general, the injection of more than 100 ml is defined as transfusion. The transfusion is administrated after mixing with another small quantity of injection.

The mixing attention flag serves to show whether any attention (by the user) is necessary or not when mixing injections. If no attention is necessary, then the mixing attention flag is "0"; if any attention is necessary because of a possible composition alteration resulting from mixing injections, then the mixing attention flag is "1"; and if there is need to solely administrate the medicament without mixing, then the mixing attention flag is "2".

The stability time after dissolution means a time for which, after dissolving the powder injection, the dissolved injection holds its stability. The reason why the injection has a state of powder is that if the medicament has a state of liquid, it has poor stability. In Table 1 therefore, the column of stability time after dissolution for the liquid medicament is blank.

The incompatibility data file stores information about an incompatibility between two kinds of injections as shown in Table 2.

TABLE 2

| Code of Medicament A | Code of Medicament B | Incompatibility Flag | Content of Composition Alteration |
|---|---|---|---|
| INJA (Injection A) | INJC (Injection C) | 0 (Δ) | After 6 hours, survival Titer 91% |
| INJA (Injection A) | INJF (Injection F) | 1 (X) | Immediately, Whited Sedimentation |

In Table 2, the incompatible flag is used to show the content of such an incompatibility. If the content is a conditional incompatibility (shown by symbol of "Δ"), then the incompatible flag is "0"; and if the content is a full incompatibility (shown by symbol of "X"), then the incompatible flag is "1". The phrase conditional incompatibility means a mixed injection that can be used within 6 hours after mixing but cannot be used after over 6 hours, which is measured from the time of mixing, has elapsed.

The attention information data file stores attention matters when using an injection as shown in Table 3.

TABLE 3

| Medicament Code | Attention Information |
|---|---|
| INJE (Injection E) | Shading should be done during drip |
| INJE (Injection E) | Watch the shock during administration |
| INJD (Injection D) | Injection velocity is to be below 50 mg per minute. |

The composition alteration record file records a generation of a situation of a composition alteration as shown in Table 4.

TABLE 4

| Terminal ID | Generation Date | Recorder | Content of Composition Alteration | Name of Generation Situation Data File |
|---|---|---|---|---|
| 0.3 | 1998.12.18 08:06 | 6007 (Yoshiko Kawamura) | Turbidity | HK03001.TXT |
| 0.5 | 1998.12.18 08:28 | 7012 (Kazuko Morimoto) | Sedi-mentation | HK05001.TXT |

The master files include a medicament master file, a patient master file, a manipulation master file, a usage master file, a ward master file, a clinic master file, a doctor master file, a nurse master file and so on. Each file stores code numbers corresponding to item names.

The input/output device 2 includes a liquid crystal display 4, a touch panel 5, a printer 6, an identification code reader (barcode reader) 7, a keyboard 8, a mouse 9 and so on.

The liquid crystal display 4 is used to display all kinds of data and so on. The liquid crystal display 4 may be replaced by a CRT display.

The touch panel 5 is provided in order to enhance the operation of inputting data. The touch panel 5 can be substituted by the liquid crystal display 4, the keyboard 8, the mouse 9 and so on.

The identification code reader 7 is used to read the identification code (barcode) of the injection prescription and the injection. The identification code is not limited to a barcode and may be a two-dimensional code of a small surface area.

The CPU 3 has an internal random-access memory (RAM) 10 to store all kinds of data and an internal read-only memory (ROM) 11 to store a control program. The CPU 3 executes a support process for injection mixing work in response to an input signal from the input/output device 2, which will be described hereinafter.

The numeral 12 designates a host computer which transmits injection prescription data to the aforementioned apparatus for supporting injection mixing work external to the apparatus.

Hereinafter, an operation of the apparatus for supporting injection mixing work will be explained in accordance with the flowchart as shown in FIG. 4.

When an operator pushes a button of "injection prescription data input" on a menu screen (not shown) displayed on the liquid crystal display 4, an injection prescription data input screen is displayed (step S1).

The injection prescription data input screen comprises, as shown in FIG. 3, columns of "patient attribute information", "date of practice", "mixing results" and "prescription", the current date, and operating buttons of "new input", "input OK", "cancel" and "end of mixing work". The column of "patient attribute information" includes a patient number, patient name and so on. In the column of "date of practice", the current date is indicated. If the desired date is inputted, the injection prescription data corresponding to the desired date is read in and displayed on the column of "prescription". In the column of "mixing results", the content of the mixing result flag for each injection prescription data is indicated. Generally, the content of the mixing result flag is "0; not mixing". If desired, "1; mixing OK" or "2; generation of composition alteration" can be inputted to be read in the specified kind of injection prescription data. In the column of "prescription", displayed is a prescription number, medicament code, medicament name, manipulation (injection manipulation: intravenous injection, intravenous drip injection, hypodermic injection, intramuscular injection), usage, and one dose rate.

All columns of the injection prescription data input screen are blank in the initial state. Thus, an input process of injection prescription data from the injection prescription file is executed (step S2).

Figure 5:
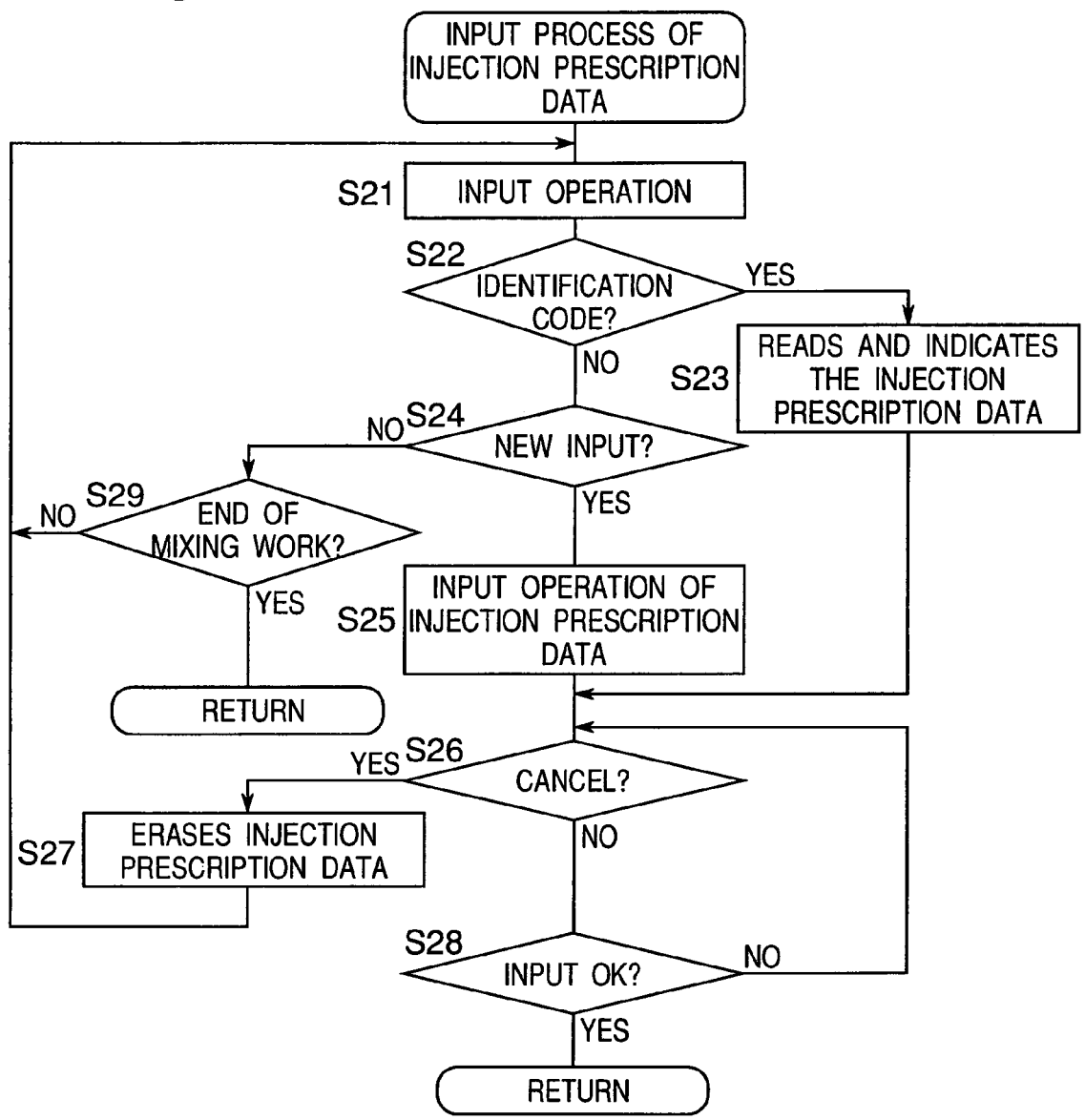
FIG. 5 is a flow chart showing an input process of injection prescription data of FIG. 4.

In the process of inputting injection prescription data, as shown in FIG. 5 the operator conducts an input operation by using the identification code reader 7, the key board 8, the mouse 9 and so on (step S21). For example, identification codes of injection prescription sheets are read by using the identification code reader 7, and operation buttons (mouse button, touch panel, etc) are operated. Then, it is judged whether or not the identification code is inputted (step S22). If the identification code is inputted, the injection prescription data corresponding to the identification code is read from the injection prescription file, whereby data corresponding to patient attribute information, as well as the injection prescription data, is indicated on the screen (step S23).

Since the injection prescription data has already been automatically read in from the host computer 12 and stored in the injection prescription data file, the injection prescription data is read from the injection prescription data file. In the injection prescription data file, as described before, only medicament codes are stored. Therefore, the formal medicament name corresponding to the medicament code is read in from the medicament master file. For example, in the case of the medicament code "INJA", the formal medicament name "injection A; 10 ml" is read in from the medicament master file.

The injection prescription sheet may be a list such as an injection work sheet. The identification code may be printed directly on the injection prescription sheet. Alternatively, a sheet on which the identification code is printed may be stuck on the injection prescription sheet. The contents of the identification code can be a patient number, an injection prescription number, an ID number of injection prescription data or so on.

On the contrary, if the identification code is not inputted, it is judged whether or not the button of "New Input" is operated (step S24). If the button of "New Input" is operated, the injection prescription data input screen is made blank. Thus, the operator can input the injection prescription data (step S25). When the patient number is inputted in the column of "patient attribute information", patient name sexuality and birth are read in from the patient master file in order to display them on the column "patient attribute information". The age of a patient is calculated based on birth and the current date and is then displayed. As to the ward, sickroom, clinic and doctor, when the operator inputs the code numbers for such information, the corresponding data is read in from the respective master file in order to display these data items. For example, when the operator inputs code "60" for the ward, data of "6 floors ward" is read in and displayed. In the same manner, when code numbers for each column are inputted, the corresponding data are read in from the respective master file so as to be displayed.

Subsequently, when the button of "cancel" is operated (step S26), each data displayed on the injection prescription data input screen is erased (step S27). When the button of "input OK" is operated instead of the button "cancel" (step S28), the process of inputting injection prescription data is terminated in order to return to the main process. When the button of "end of mixing work" is operated because of no injection prescription data (step S29), the input process of inputting injection prescription data is terminated in order to return to the main process. Thus, the injection prescription data input screen is changed to the menu screen.

When the button of "input OK" on the screen of "injection prescription data input", as shown in FIG. 3, is operated to terminate the input process of prescription data as shown in FIG. 5, a screen of "injection mixing support", as shown in FIG. 10, is displayed (step S3). In this screen, the column of "patient attribute information" (patient number to doctor) is first displayed. The injection prescription data which has the mixing result flag of "not mixing" is read in from the injection prescription file (step S4).

Thus, in accordance with the injection prescription data read in at the step S4, decision process of injection mixing order is executed (step S5).

In the decision process of the injection mixing order, as shown in FIG. 6, after acquiring pH values of medicaments from the mixing work supporting data file by using the medicament codes as a search key, the medicaments are rowed in order in accordance with the pH values thereof (step S31). The medicament of transfusion is moved to the forefront (step S32). If there are a plurality of medicaments of transfusion, the medicaments are moved to the forefront keeping the order of pH values as it is. Then, the medicament corresponding to a sole administration is moved to the rear (step S33). In this embodiment, the medicament with the mixing attention flag of "sole administration" is moved to the rear. If there are a plurality of medicaments of sole administration, in the same manner as in the case of a plurality of medicaments of transfusion, the medicaments are moved to the rear keeping the order of pH values as it is. Thus, the mixing order of the remaining medicaments which are not moved is decided (step S34).

After the mixing order of the medicaments within the injection prescription data is decided in the decision process of injection mixing order as described above, the mixing order is indicated on the screen of "injection mixing support" as shown in FIG. 10 and printed by the printer 6 (step S6). In this stage, the columns of "incompatibility" and "number" are blank.

Subsequently, a decision process of the incompatibility of injections is executed (step S7).

In the decision process of the incompatibility of injections, as shown in FIG. 7, it is judged whether or not the medicaments with the mixing order decided as described above are incompatible in accordance with the incompatible combination stored in the incompatibility data file (step S41). If there is an incompatible combination (step S42), data corresponding to the incompatible combination is read in from the incompatibility data file (step S43).

The contents of the data corresponding to the incompatible combination are indicated on a screen showing a content of a composition alteration, which is a different window from the screen of "injection mixing support" as shown in FIG. 10 (step S8). The content of composition alteration can be printed by pressing the button of "print". The content of incompatibility is indicated by the symbols "Δ" or "X" in the column of "incompatibility" on the screen of "injection mixing support".

After the decision process of incompatibility of injections is terminated, the attention information is obtained from the attention information data file (step S9). Then, the attention information is indicated on a attention information screen as shown in FIG. 13 (step S10). The order of the indication is the same as in the decision process of the mixing order (step S5). The indicated attention information can be printed by pressing the button of "print".

After completion of preparation for mixing the injections, a management process of a mixing-work progress situation is executed (step S11).

In the management process of the mixing-work progress situation, as shown in FIGS. 8 and 9, the medicament to be mixed is indicated by marking "★" on the beginning of the line (step S51) and reversing the representation of the line. Thus, the operator can recognize the medicament to be mixed at a glance.

Then, the operator conducts an input operation of injections which are used in the mixing work (step S52). In this input operation, the operator can read the identification code of the medicaments (injections) to be mixed by using the identification code reader 7 and operating the operation buttons (mouse button, touch panel, etc). Then, it is judged whether or not the identification code is inputted (step S53). If the identification code is inputted, then it is judged whether or not the medicament with the identification code inputted is in conformity with the medicament indicated at step S51 (step S54). If NO, a nonconformity error is indicated (step S55). If YES, the number indicated on the column of "number" is incremental and it is judged whether or not the number reaches the specified mixing number (step S56). If NO, the flow is returned to step S52 to repeat the same process until the number reaches the specified mixing number. For example, as the mixing number of the injection A as shown in FIG. 10 is two, the process is repeated twice. The operator (nurse) proceeds the mixing work of the medicaments for each time when he/she confirms the conformity.

If the number reaches the specified mixing number, it is judged whether or not the input process of the medicaments to be mixed is finished (step S57). If NO, the next medicament to be mixed is indicated (step S58). The sequential process is executed until the input and mixing process of all medicaments to be mixed is finished. If the input and mixing process of all medicaments to be mixed is finished, it is confirmed that a button of "record of composition alteration" is not operated, and then the mixing result flag of the injection prescription data in the injection prescription file is set to "mixing OK" (step S59).

On the other hand, if the identification code of the medicament to be mixed is not inputted at step S53, the operation buttons on the injection mixing support screen of FIG. 10 are operated due to the operator's own discrimination.

Thus, it is judged whether or not the button of "go to next medicament" is operated (step S60). For example, in the case where the reading is out because the identification code reveals an undesirable medicament, the operator can operate the button of "go to next medicament" to proceed to the next medicament. If it is judged that the button is operated, then the flow is returned to step S57 and the same process is repeated. In the case where it has been already confirmed that the mixing is proper (OK) because of the same combination of injections, the operator can operate the button of "mixing OK". If it is judged that the button is operated (step S61), then the flow is returned to step S59 and the same process is repeated.

In the case where the mixing is not proper because the composition alteration is caused during mixing of the medicaments, the operator can operate the button of "record of composition alteration". If it is judged that the button is operated (step S62), a screen of a record of the composition alteration, as shown in FIG. 14, is displayed. Then, the operator inputs the content (comment) of the composition alteration (step S64) and operates the button of "record OK". Thus, the content of the composition alteration inputted by the operator is written in the composition alteration record file (step S65). Subsequently, the mixing result flag of the injection prescription data in the injection prescription file is set to "generation of composition alteration" (step S66). At this stage, only the fact that the composition alteration is caused due to the combination of plural injections contained in the injection prescription data is recorded. Afterward, an experiment is conducted on the basis of the record. As a result, if a combination of two kind of injections causes the composition alteration, such a combination can be specified, and the combination is recorded in the incompatibility data file.

In the case where the record of composition alteration is not desired, the operator can operate the buttons of "cancel" or "end of mixing work". If it is judged that the button is operated (step S63), the management process of a mixing-work progress situation is compulsorily terminated. When the button of "end of mixing work" is operated, the injection mixing support screen is changed to the menu screen. By operating the button of "print", the content of the injection mixing support screen can be printed.

According to the management process of the mixing-work progress situation it is possible to surely confirm whether or not the selected injection is in conformity with the indicated injection.

Finally, it is judged whether or not all of the injection prescription data for the present patient are treated (step S112). If NO, the flow is returned to step S4 and the same process is repeated with respect to the next injection prescription data. If YES, the flow is returned to step S1 and the same process is repeated with respect to the next patient.

In the case where a plurality of prescriptions is issued for one patient, the column of "prescription" of the injection prescription data input screen is shown in FIG. 11.

The CPU 3, the liquid crystal display 4, the keyboard 8, the mouse 9 and memory device 1 in the above described embodiment can be substituted by a personal computer. The memory device 1 may be an independent file server (with a CPU built-in). The system may be a client/server architecture in which the CPU 3, as a client terminal, is connected to the server via the network (LAN). For example, the server is disposed in a medicine information office of a medicament division of hospital, and a plurality of client terminals are disposed in each nurse station of the ward. According to this arrangement, all data which the apparatus needs for supporting injection mixing work can be controlled by the nurse through the server.

Although the present invention has been fully described by way of the examples with reference to the accompanying drawings, it is to be noted here that various changes and modifications will be apparent to those skilled in the art. Therefore, unless such changes and modifications otherwise depart from the spirit and scope of the present invention, they should be construed as being included therein.

What is claimed is:

1. An apparatus for supporting injection mixing work, said apparatus comprising:
   an acquisition unit operable to acquire an injection prescription data including data specifying a plurality of injections which are prescribed to a patient; a memory unit operable to store corresponding relations between the data specifying the plurality of injections and pH-values data of the plurality of injections for deciding a mixing order of the plurality of injections before dosing the plurality of injections to a patient;
   a decision unit operable to decide a proper mixing order of the plurality of injections included in the injection prescription data acquired by said acquisition unit based on the pH-values data for deciding a mixing order corresponding to the data specifying the plurality of injections stored in said memory unit; and
   a display unit operable to display an indication representing the mixing order decided by said decision unit;
   wherein the decided mixing order displayed by said display unit is used to properly combine a plurality of the injections which are prescribed to the patient.

2. The apparatus for supporting injection mixing work according to claim 1, wherein:
   said memory unit is further operable to store corresponding relations between the data specifying the plurality of injections and data identifying whether or not the plurality of injections are transfusions; and said decision unit is operable to decide the proper mixing order of the plurality of injections based on the pH-values data for deciding the mixing order corresponding to the data specifying the plurality of injections, and the data identifying whether or not the injections are transfusions.

3. The apparatus for supporting injection mixing work according to claim 2, wherein:
said memory unit is further operable to store corresponding relations between the data specifying the plurality of injections and data identifying whether or not the plurality of injections need sole administration; and
said decision unit is operable to decide the proper mixing order of the plurality of injections based on the pH-values data for deciding the mixing order corresponding to the data specifying the plurality of injections, the data identifying whether or not the injections are transfusions, and the data identifying whether or not the injections need sole administration.

4. The apparatus for supporting injection mixing work according to claim 3, wherein:
for the injections requiring transfusions, said display unit is operable to display an indication representing that the name of the injection is a transfusion; and
for the injections in need of sole administration, said display unit is operable to display an indication representing that the injection needs sole administration.

5. The apparatus for supporting injection mixing work according to claim 1, wherein:
said memory unit is further operable to store corresponding relations between the data specifying the plurality of injections and data identifying whether or not the plurality of injections need sole administration; and
said decision unit is operable to decide the proper mixing order of the plurality of injections based on the pH-values data for deciding the mixing order corresponding to the data specifying the plurality of injections, and the data identifying whether or not the injections need sole administration.

6. The apparatus for supporting injection mixing work according to claim 1, wherein:
said memory unit is further operable to store corresponding relations between a combination of injections and data showing a degree to which the combination of injections is improper;
said apparatus further includes a judging unit operable to judge whether or not any improper combination is present for the injections included in the injection prescription data acquired based on the corresponding relations between combination of injections and data showing the degree to which the combination of injections is improper; and
for the injections which are judged to be an improper combination by said judging unit, said display unit is operable to display an indication showing the degree to which the combination of the injections is improper.

7. The apparatus for supporting injection mixing work according to claim 6, further comprising an operation unit operable to record the corresponding relations between combination of injections and data showing a degree to which the combination of injections is improper onto said memory unit.

8. The apparatus for supporting injection mixing work according to claim 1, wherein:
said memory unit is further operable to store corresponding relations between the data specifying the plurality of injections and matters requiring attention when using the injections; and
said display unit is operable to display the matters requiring attention when using the injections corresponding to the data specifying the plurality of injections.

9. The apparatus for supporting injection mixing work according to claim 1, wherein the indication representing the mixing order decided by said decision unit includes names of the plurality of injections included in the injection prescription data acquired by said acquiring unit.

10. The apparatus for supporting injection mixing work according to claim 9, wherein said display unit is operable to display an indication for identifying the name of an injection as to the injection to be mixed subsequently.

11. The apparatus for supporting injection mixing work according to claim 1, wherein the indication representing the mixing order decided by said decision unit includes an indication representing that the injection included in the injection prescription data acquired by said acquiring unit is a transfusion.

12. The apparatus for supporting injection mixing work according to claim 1, wherein the indication representing the mixing order decided by said decision unit includes an indication representing that the injection included in the injection prescription data acquired by said acquiring unit needs sole administration.

13. The apparatus for supporting injection mixing work according to claim 1, wherein the indication representing the mixing order decided by said decision unit includes an indication representing that the injections included in the injection prescription data acquired by said acquiring unit are not a proper combination.

14. The apparatus for supporting injection mixing work according to claim 1, further comprising:
an input unit operable to input data specifying injections to be mixed subsequently; and
a comparison unit operable to compare the data specifying injections inputted with the data specifying injections to be mixed subsequently;
wherein said display unit is operable to display an indication that the comparison by said comparison unit results in an inconsistence.

15. The apparatus for supporting injection mixing work according to claim 1, further comprising:
an operation unit operable to operate to record a composition alteration; and
a recorder operable to record the composition alteration.

16. The apparatus for supporting injection mixing work according to claim 15, wherein when said operation unit is operated, said recorder is operable to record a fact that the composition alteration is caused due to the combination of the plurality of injections.

17. The apparatus for supporting injection mixing work according to claim 15, wherein when said operation unit is operated, the composition alteration caused due to the combination of the plurality of injections specified by the data specifying a plurality of injections is set to a mixing result flag.

* * * * *